United States Patent
Ikeda

Patent Number: 5,861,402
Date of Patent: Jan. 19, 1999

[54] 1,4-DIHYDROPYRIDINE COMPOUNDS

[75] Inventor: Takafumi Ikeda, Handa, Japan

[73] Assignee: Pfizer Pharmaceuticals, Inc., Tokyo, Japan

[21] Appl. No.: 797,681

[22] Filed: Jan. 31, 1997

[30] Foreign Application Priority Data

Feb. 19, 1996 [WO] WIPO .................. PCT/IB96/00131

[51] Int. Cl.⁶ .................. C07D 401/06; A61K 31/495
[52] U.S. Cl. .................. 514/252; 514/255; 544/365; 544/362
[58] Field of Search .................. 544/365, 362; 514/252, 255

[56] References Cited

U.S. PATENT DOCUMENTS

| | | | |
|---|---|---|---|
| 5,162,497 | 11/1992 | Coy et al. | 530/314 |
| 5,610,142 | 3/1997 | Mavunkel et al. | 514/16 |

OTHER PUBLICATIONS

Principles of Psychopharmacology Academic Press Clark et al. p. 166, 1970.

*Primary Examiner*—Jane Fan
*Attorney, Agent, or Firm*—Peter C. Richardson; Paul H. Ginsburg; Mark Dryer

[57] ABSTRACT

A compound of the formula:

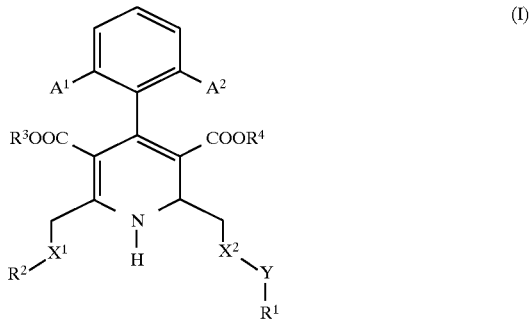

and its pharmaceutically acceptable salts, wherein $A^1$ and $A^2$ are each halo or H; $X^1$ is $CH_2$, CO, SO or $SO_2$; $X^2$ is $CH_2$ or CO; Y is piperazinyl-$(CH_2)_n$—, 2,3,4,5,6,7-hexahydro-1H-1,4-diazepinyl-$(CH_2)_n$—or —$N(R^5)$—$(CH_2)_n$— wherein $R^5$ is H or $C_{1-4}$ alkyl, and n is 0, 1, 2, 3, or 4; $R^1$ is selected from the following: (a) N-morpholino-$C_{1-4}$ alkylphenyl, $C_{1-4}$ alkoxycarbonyl, $C_{2-5}$ acyl, dihydroimidazolyl, formamidino, guanidino or dihydroimidazolylamino, etc.; (b) hydrogen, $C_{1-4}$ alkyl, etc.; (c) piperidinyl; (d) $C_{5-14}$ cycloalkyl, bicycloalkyl or tricycloalkyl; (e) $C_{7-14}$ azacyclo-, azabicyclo- or azatricycloalkyl; and (f) $C_{7-10}$ bicycloalkenyl, benzo $C_{5-7}$ cycloalkyl or heterocyclic, etc., with proviso that when Y is piperazinyl, at least one of $A^1$ and $A^2$ is H; $X^2$ is $CH_2$; and/or $R^1$ is a group selected from group (a); $R^2$ is hydrogen, $C_{1-4}$ alkyl, optionally substituted phenyl, or heterocyclic; and $R^3$ and $R^4$ are each $C_{1-5}$ alkyl. The novel dihydropyridine compounds of this invention have excellent bradykinin antagonistic activity and are thus useful for the treatment of inflammation, cardiovascular disease, pain, common cold, allergies, asthma, pancreatitis, burns, virus infection, head injury, multiple trauma or the like in mammalian, especially humans.

15 Claims, No Drawings

1,4-DIHYDROPYRIDINE COMPOUNDS

TECHNICAL FIELD

This invention relates to novel 1,4-dihydropyridine compounds, and more particularly to 1,4-dihydropyridine compounds having a substituted or unsubstituted-carbamoylmethyl group attached to the 2-position of the dihydropyridine ring. These compounds are useful as antagonists of bradykinin, and are thus useful in the treatment of inflammation, cardiovascular disease, pain, common cold, allergies, asthma, pancreatitis, burns, virus infection, head injury, multiple trauma or the like in mammalia, especially humans. The present invention also relates to a pharmaceutical composition useful in the treatment of the above clinical conditions, which comprises the 1,4-dihydropyridine compound of the invention and a pharmaceutically acceptable carrier.

BACKGROUND ART

Bradykinin ("BK") is generated under normal conditions in mammalia by the action of various plasma enzymes such as kallikrein on high molecular weight kininogens. It is widely distributed in mammals, as are its two receptor subtypes, $B_1$ and $B_2$. The actions of BK at the $B_1$ receptor include mainly contraction of arterial and venous preparations, although it can cause relaxation of peripheral resistance vessels as well.

Many of the more important functions of BK, such as increases in vascular permeability, pain, and vasodilatation, however, are mediated by the $B_2$ receptor. These effects at the $B_2$ receptor are believed to be responsible for BK's role in numerous diseases, such as inflammation, cardiovascular disease, pain, and the common cold. Hence antagonists at the $B_2$ receptor should find considerable therapeutic applications. Most of the efforts in this area thus far have been directed at peptidic analogues of the BK structure, some of which have been studied as analgesics and antiinflammatory agents.

It would be desirable if there were provided a non-peptide antagonist of the $B_2$ receptor, having a good $B_2$ antagonistic activity and a good metabolic stability.

BRIEF DISCLOSURE OF THE INVENTION

The present invention provides a compound of the formula:

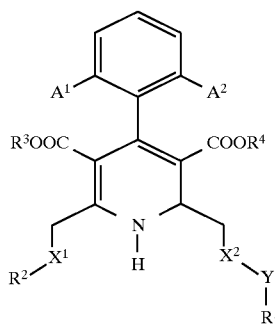

(I)

and its pharmaceutically acceptable salts, wherein $A^1$ and $A^2$ are each halo or H; $X^1$ is $CH_2$, CO, SO or $SO_2$; $X^2$ is a direct bond $CH_2$ or CO; Y is piperazinyl-$(CH_2)_n$—, 2,3,4,5,6,7-hexahydro-1H-1,4-diazepinyl-$(CH_2)_n$— or— $N(R^5)$—$(CH_2)_n$— wherein $R^5$ is H or $C_{1-4}$ alkyl, and n is 0, 1, 2, 3, or 4; $R^1$ is selected from the following:

(a) N-morpholino-$C_{1-4}$alkylphenyl, $C_{1-4}$ alkoxycarbonyl, $C_{2-5}$acyl, 4,5-dihydroimidazolyl, formamidino, guanidino or dihydroimidazolylamino, optionally substituted with one or two substituents selected from $C_{1-4}$ alkyl, hydroxy and amino;

(b) hydrogen, $C_{1-4}$ alkyl optionally substituted with one or two substituents selected from hydroxy, amino, $C_{1-4}$ alkylamino, di-$C_{1-4}$ alkylamino, pyridyl, carbamoyl, pyrrolidinocarbonyl, propylaminocarbonyl, piperidinocarbonyl or morpholinocarbonyl;

(c) piperidinyl optionally substituted on the nitrogen atom with $C_{1-4}$ alkyl or $C_{1-4}$alkoxycarbonyl;

(d) $C_{5-14}$ cycloalkyl, bicycloalkyl or tricycloalkyl, optionally substituted with one or two substituents selected from oxo, hydroxy, amino, guanidino, $C_{1-4}$ alkylamino, di-$C_{1-4}$ alkylamino, methoxybenzamido or morpholino;

(e) $C_{7-14}$ azacyclo-, azabicyclo- or azatricyclo alkyl, in which the nitrogen atom optionally has a substituent selected from $C_{1-4}$ alkyl, formamidino, dihydroimidazolyl, benzyl optionally substituted with one or two substituents selected from halo and trihalo $C_{1-4}$ alkyl, $C_{1-4}$ alkyloxycarbonyl optionally substituted with one or two halogen atoms and $C_{2-5}$ acyl; and (f) $C_{7-10}$ bicycloalkenyl, benzo $C_{5-7}$ cycloalkyl or heterocyclic; as hereinafter defined with proviso that when Y is piperazinyl, (i) at least one of $A^1$ and $A^2$ is H; $X^2$ is $CH_2$ or $R^1$ is a group selected from group (a); (ii) at least one of $A^1$ and $A^2$ is H and $X^2$ is $CH^2$, (iii) at least one of $A^1$ and $A^2$ is H and $R^1$ is a group selected from (a); (iv) X is $CH^2$ and $R^1$ is a group selected from (a); or (v) at least one of $A^1$ and $A^2$ is H, $X^2$ is $CH^2$ and $R^1$ is a group selected from (a); $R^2$ is hydrogen, $C_{1-4}$ alkyl, phenyl optionally substituted with one or two substituents selected from halo, $C_{1-4}$ alkyl, trihalo $C_{1-4}$ alkyl and $C_{1-4}$ alkoxy, or heterocyclic; and $R^3$ and $R^4$ are each $C_{1-5}$ alkyl.

The dihydropyridine compounds of this invention have excellent bradykinin antagonistic activity and are thus useful for the treatment of inflammation, cardiovascular disease, pain, common cold, allergies, asthma, pancreatitis, burns, virus infection, head injury, multiple trauma or the like in mammalia, especially humans.

The present invention also provides a pharmaceutical composition for the treatment of medical conditions caused by bradykinin such as inflammation, cardiovascular disease, pain, common cold, allergies, asthma, pancreatitis, burns, virus infection, head injury, multiple trauma or the like, which comprises a therapeutically effective amount of the dihydropyridine compound of formula (I) or its pharmaceutically acceptable salt together with a pharmaceutically acceptable carrier.

The present also provides a method for the treatment of disease conditions caused by bradykinin, in a mammalian subject, which comprises administering to said subject a therapeutically effective amount of a compound of formula (I).

DETAILED DESCRIPTION OF THE INVENTION

As used herein, the term "$C_{1-4}$ alkylamino" and by "$C_{1-4}$ dialkylamino" mean $N(R')R''$, wherein R' is hydrogen or $C_{1-4}$ alkyl and R" is $C_{1-4}$ alkyl, such as methylamino, ethylamino, n-propylamino, isopropylamino, p-butylamino, t-butylamino, dimethylamino, diethylamino and ethylmethylamino;

the term "$C_{5-14}$ cycloalkyl, bicycloalkyl or tricycloalkyl" means monocyclic, bicyclic or tricyclic alkyl having 5 to 14 carbon atoms, such as cyclopentyl, cycloheptyl, cyclooctyl, bicyclo[3.2.1]octyl, bicyclo[3.3.0]octyl and tricyclo[4.3.3.0]dodecyl;

the term "$C_{7-14}$ azacyclo-, azabicyclo- or azatricycloalkyl" means monocyclic, bicyclic or tricyclic alkyl having 7 to 14 carbon atoms and one nitrogen atom in the ring, such as quinuclidinyl, azabicyclo[3.2.1]octyl, azabicyclo[3.3.1]nonyl, and azatricyclo[3.3.3.0]undecyl; and the term "heterocyclic" means a monocyclic or bicyclic hydrocarbon group which has one or more hetero atoms in the ring, preferably has 4 to 10 carbon atoms and 1 to 3 heteroatoms, including piperidino, morpholino, thiamorpholino, pyrrolidino, pyrazolino, pyrazolidino, pyrazoryl, piperazinyl, furyl, thienyl, oxazolyl, tetrazolyl, thiazolyl, imidazolyl, imidazolinyl, pyrazolyl, pyridyl, pyrimidinyl, pyrrolyl, pyrrolidinyl and quinolyl.

In the above (I), preferably, $R^1$ is selected from group (a); $R^2$ is hydrogen, $C_{1-4}$ alkyl or phenyl optionally substituted with one or two substituents selected from halo, $C_{1-4}$ alkyl, trihalo $C_{1-4}$ alkyl and $C_{1-4}$ alkoxy; and $R^3$ and $R^4$ are each $C_{1-3}$ alkyl.

Among these, more preferably $X^1$ is $CH_2$ or CO; $R^1$ is N-morpholinomethylphenyl, t-butoxycarbonyl, acetyl, guanidinopropyl, 4,5-dihydroimidazole-2-propyl, 4,5-dihydroimidazol-2-yl or guanidinoethyl.

Furthermore in the above formula (I), $A^1$ and $A^2$ may be the same as or different from each other, and are selected from chloro, bromo, iodo and fluoro, preferably chloro and bromo.

In the above formula (I), $X^1$ is preferably a direct bond or $CH_2$

In the above formula (I), examples of $R^1$ selected from group (b) are hydrogen, pyridyl, pyrrolidinylcarbonyl, propylaminocarbonyl, hydroxyethyl and dimethylaminopropyl.

Examples of $R^1$ selected from group (c) are piperidinyl, 1-(butoxycarbonyl)piperidinyl and 1-methylpiperidinyl.

Examples of $R^1$ selected from group (d) are $C_{5-6}$ cycloalkyl, bicyclo[3.2.1]octyl and one of the following:

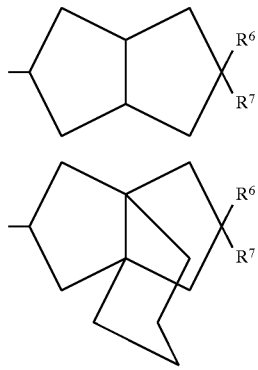

(wherein $R^6$ is hydrogen and $R^7$ is hydroxy, amino, methoxybenzamido or morpholino, or $R^6$ and $R^7$ are taken together to represent an oxo group).

Examples of $R^1$ selected from group (e) are the following groups:

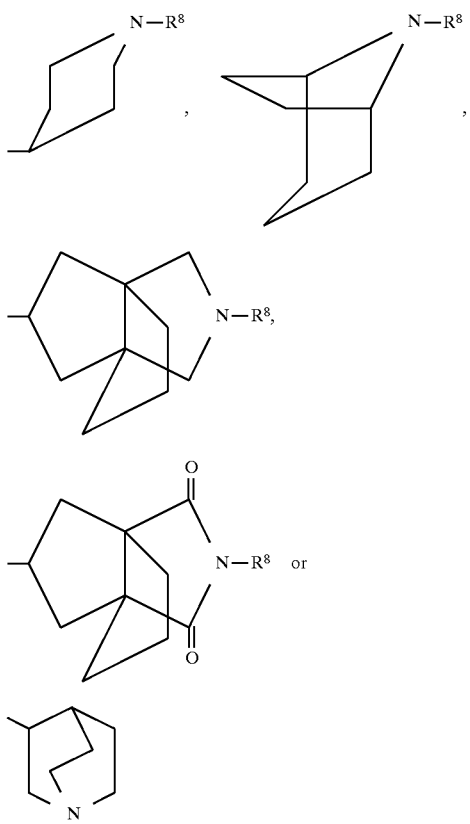

(wherein $R^8$ is hydrogen, formamidino, 4,5-dihydroimidazole-2-yl, $C_{1-4}$ alkyl, benzyl optionally substituted with one or two substituents selected from halo and trihaloalkyl, acetyl or chloroethoxycarbonyl).

Examples of $R^1$ selected from group (f) are norbornenyl, indanonyl, quinuclidinyl or pyrimidinyl.

In the above formula (I), examples of $R^2$ are hydrogen, phenyl, methoxyphenyl, propyl(methoxy)phenyl, methylphenyl, chlorophenyl, pyridyl and thienyl.

In the above formula (I), examples of $R^3$ and $R^4$ are methyl, ethyl, propyl, t-butyl, s-butyl and pentyl, preferably $C_{1-3}$ alkyl such as methyl and ethyl.

Of these compounds, the preferred compounds are: dimethyl 4-(2,6-dichlorophenyl)-2-[4-(3-guanidinopropyl)-1-piperazinyl]carbonylmethyl-6-(2-phenylethyl)-1,4-dihydropyridine-3,5-dicarboxylate dihydrochloride; dimethyl 4-(2,6-dichlorophenyl)-2-{4-[3-(4,5-dihydroimidazole-2-yl)propyl]1-piperazinyl}carbonylmethyl-6-(2-phenylethyl)-1,4-dihydropyridine-3,5-dicarboxylate hydrochloride, hydriodide; dimethyl 4-(2,6-dichlorophenyl)-2-[4-(4,5-dihydroimidazole-2-yl)-1-piperazinyl]carbonylmethyl-6-(2-phenylethyl)-1,4-dihydropyridine-3,5-dicarboxylate hydriodide; and dimethyl 4-(2,6-dichlorophenyl)-2-[4-(2-guanidinoethyl)-1-piperazinyl]carbonylmethyl-6-(2-phenylethyl)-1,4-dihydropyridine-3,5-dicarboxylate dihydrochloride.

General Synthesis

The dihydropyridine compounds of formula (I) of this invention may be prepared by a variety of synthetic methods known to those skilled in the art. For example, the dihydropyridine compounds of formula (I), wherein $X^2$ is CO and Y is 1,4-piperazinyl-$(CH_2)_n$— or —$N(R^5)$—$(CH_2)_n$—, may be prepared by reaction of compound (II) with compound (III-a) or (III-b), followed, if desired, by conversion of a compound in which $R^1$ is H into a compound in which $R^1$ is other than H, as indicated in the following Preparation Method A–I.

Preparation Method A-I:

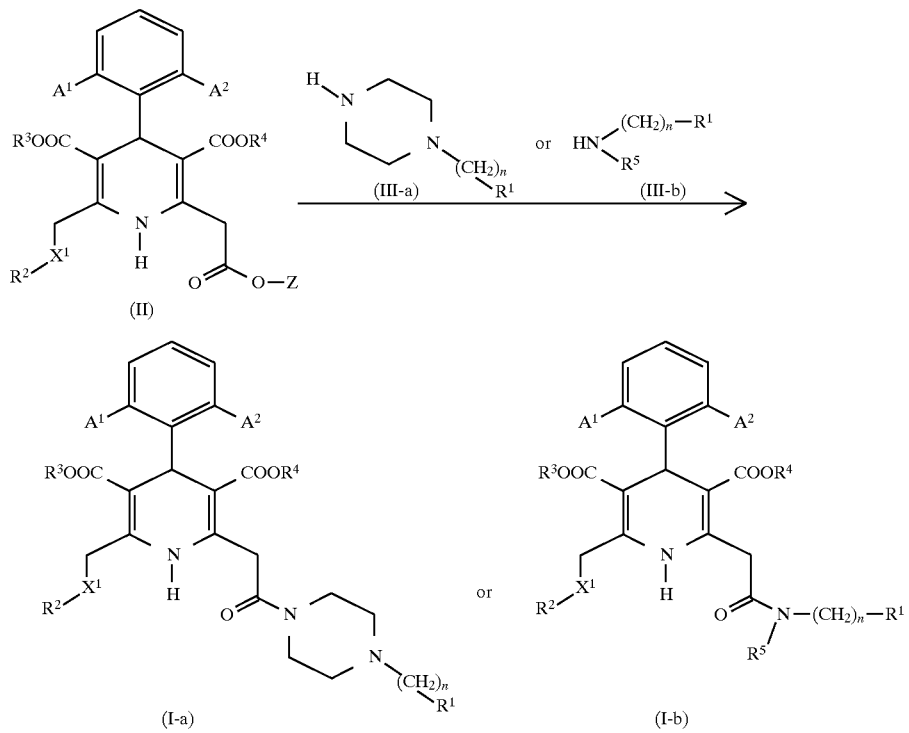

(wherein Z is hydrogen or lower alkyl such as methyl and ethyl; and the other symbols are as already defined, with proviso that $X^1$ is $CH_2$, protected carbonyl, sulfide or sulfoxide)

In Preparation Method A–I, when Z is lower alkyl, the compound (II) may be first subjected to selective saponification of the ester residue at the 2-position of the compound (II), followed by acidification to afford a free acid, which is coupled with the compound (III-a) or (III-b) to give the dihydropyridine compound (I-a) or (I-b). In this case, when $X^1$ is carbonyl, the carbonyl may be protected by a conventional protecting group which is removed in an appropriate step by conventional means. A suitable protecting group for a carboxy group is, for example, a $C_{1-4}$ alkyl (especially methyl or ethyl) which may be removed by hydrolysis with a suitable base such as an alkali metal hydroxide (e.g., lithium or sodium hydroxide). When Z is H, the compound (II) may be directly coupled with the compound (III-a) or (III-b) to obtain the dihydropyridine compounds (I-a) or (I-b).

The selective saponification and the acidification may be carried out by conventional procedures. In a typical procedure, the selective saponification is carried out by treatment with 2N sodium hydroxide in aqueous methanol. In a typical procedure, the acidification is carried out by treatment with 1N hydrochloric acid in a suitable reaction-inert solvent.

The coupling reaction between the obtained acid and the compounds of the formula (III-a) or (III-b) may be carried out in a reaction-inert solvent as listed above (preferably dichloromethane) using a coupling agent such as dicyclohexylcarbodiimide (DCC), water soluble carbodiimide (WSCD), 2-ethoxy-N-ethoxycarbonyl-1,2-dihydroquinoline, Bop agent (Benzotriazol-1-yloxy-tris (dimethylamino)phosphonium hexafluorophosphate), diethyl azodicarboxylate-triphenylphosphine, diethylcyanophosphonic acid and diphenylphospholylazide. This reaction may be carried out at a temperature in the range from –30° to 40° C., usually from 0° C. to 25° C. for 10 minutes to 96 hours, usually 30 minutes to 24 hours.

A compound (I-a) or (I-b) wherein $R^1$ is other than H and n is 0, can be obtained from the corresponding compound (I-a) or (I-b) wherein $R^1$ is H, by reductive alkylation of the terminal nitrogen with appropriate aldehyde or ketone. The reductive alkylation may be carried out in a suitable reaction-inert solvent, in the presence of a suitable reducing agent such as $NABH_4$, $NaBH_3CN$ or $NaBH(OAc)_3$ at a temperature in the range from –20° to 120° C., usually 0 to 80° C. for 10 minutes to 1 week, usually 30 minutes to 96 hours, optionally in the presence of molecular sieves.

In addition, the compounds of the formula (III-a) and (III-b) as used herein may be either known or may be prepared by known methods. For example, the 4-N-substituted piperazines (wherein n is 0) may be prepared by means of (1) N alkylation of 4-N-protected piperazine with appropriate alkyl halide, $R^1$-halo, or (2) reductive amination of 4-N-protected piperazine with appropriate aldehyde or ketone in the presence of a reducing agent, followed by deprotection of the amino-protecting group. Suitable amino-protecting groups include, for example, benzyl, benzyloxycarbonyl and t-butoxycarbonyl group. Suitable reducing agents include, for example, sodium cyanoborohydride, aluminum-based reducing reagents, boranes, borohydrides or trialkylsilanes. After finishing introduction of a desired $R^1$ group, the amino-protecting group is removed by a suitable standard procedure to provide the objective compound. When a compounds of the formula (I) wherein Y is 2,3,4,5,6,7-hexahydro-1H-1,4-diazepinyl-$(CH_2)_n$—, is required, 2,3,4,5,6,7-hexahydro-1H-1,4-diazepinyl-$(CH_2)_n$—$R^1$ is used instead of the compound of the formula (III-a).

Preparation Method A-II

The compounds of formula (I) wherein $X^2$ is $CH_2$ may be prepared by the following method.

paraformaldehyde in acetic acid. These reaction may be carried out at a temperature in the range from −10° to 50° C., usually from 0° C. to 40° C. for 30 minutes to 24hours, usually 1 hour to 8 hours. The selective saponification and the acidification may be carried out by conventional procedures. In a typical procedure, the selective saponification is carried out by treatment with 2N sodium hydroxide in 1,4-dioxane. In a typical procedure, the acidification is carried out by treatment with 1N hydrochloric acid in a suitable reaction-inert solvent. These reaction may be car-

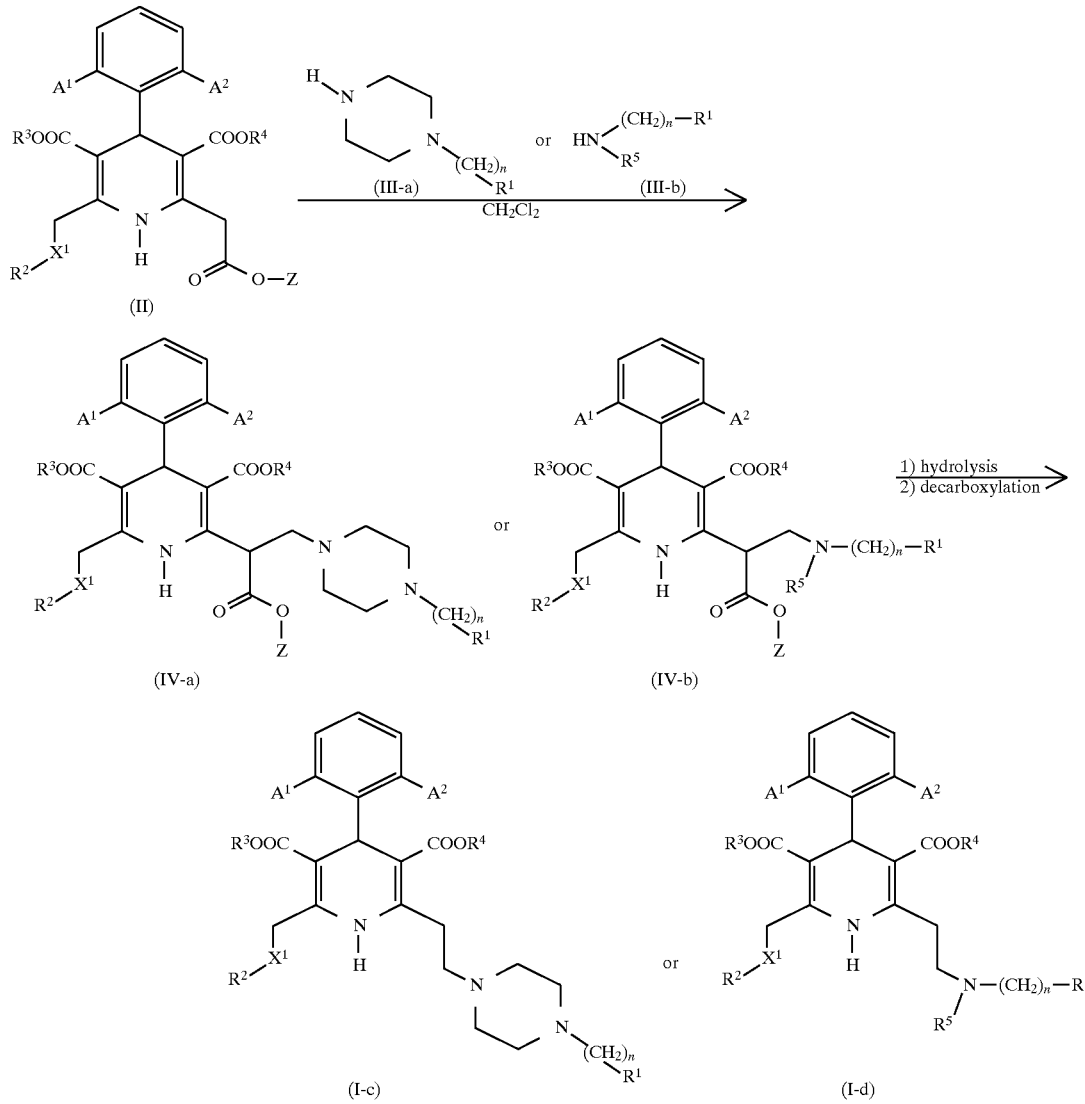

In Preparation Method A-II, when Z is lower alkyl, the compound (II) may be first subjected to Mannich type alkylation of the dichloromethane at the 2-position of the compound (II) to give the adduct (IV-a) or (IV-b). The adduct (IV-a) or (IV-c) were subjected to selective saponification of the ester residue of the 2-position, followed by acidification to afford a free acid. The corboxylic acid is heated in an inert solvent to give the corresponding decarboxylated compound (I-c) or (I-d). Mannich type reaction may be carried out by conventional procedures. In a typical procedure, the Mannich alkylation may be carried out by treatment with, for example, 4-alkylpiperazine and ried out at a temperature in the range from 5° to 50° C., usually from 15° C. to 30° C. for 10 minutes to 2 hours, usually 20 minutes to 1 hour. The decarboxylation may be carried out by conventional procedures. In a typical procedure, the carboxylic acid is heated in a reaction inert solvent, (preferably toluene) at a temperature in the range from 70° to 140° C. usually from 90° C. to 110° C. for 15 minutes to 4 hours, usually 30 minutes to 2 hours. When a compound of the formula (I) wherein Y is 2,3,4,5,6,7-hexahydro-1H-1,4-diazepinyl-$(CH_2)_n$—, is required, 2,3,4,5,6,7-hexahydro-1H-1,4-diazepinyl-$(CH_2)_n$—$R^1$ is used instead of the compound of the formula (III-a).

The compound (II) may be prepared by several methods as indicated in the following Preparation Methods B-I to B-III.

Preparation Method B-I:

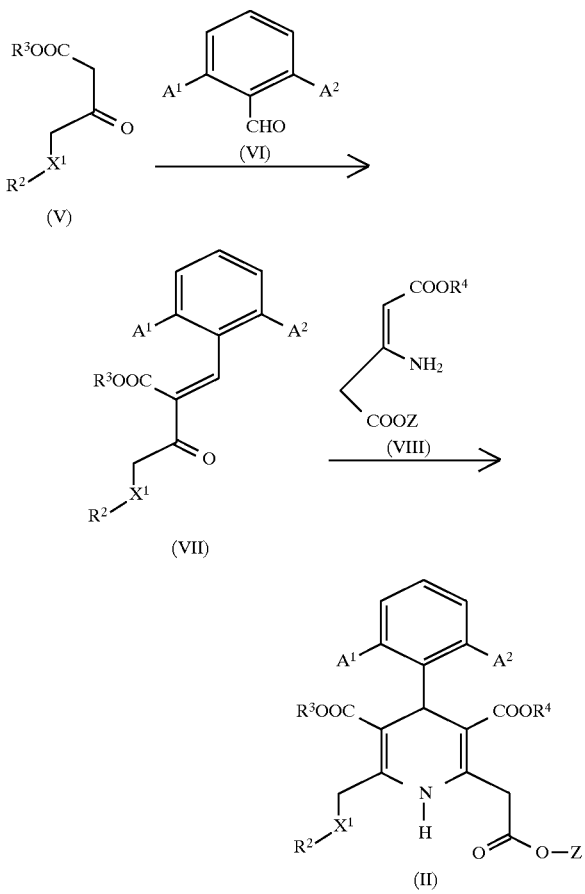

(wherein Z is hydrogen or lower alkyl such as methyl and ethyl; and the other symbols are as already defined, with proviso that $X^1$ is $CH_2$, protected carbonyl, sulfide or sulfoxide)

This method utilizes the modified Hantzsch synthesis as described in A. Sausins and G. Duburs, *Heterocycles*, 1988, 27, 269. In this method, beta-keto ester (V) is first reacted with substituted benzaldehyde (VI) to obtain compound (VII). This reaction may be carried out in a suitable reaction-inert solvent. Suitable solvents include, for example, aromatic hydrocarbons such as benzene, toluene and xylene; alcohols such as methanol, ethanol, propanol and butanol; ethers such as ethyl ether, dioxane and tetrahydrofuran; halogenated hydrocarbons such as methylene chloride, chloroform and dichloroethane; amides such as N,N-dimethylformamide; and nitrites such as acetonitrile. This reaction may be carried out at a temperature of 0° C. to 200° C., preferably from 80° C. to 120° C. for 30 minutes to 24 hours, preferably 30 minutes to 6 hours. If desired, this reaction may be catalyzed by a base such as piperidine, pyridine or alkoxide, or by an acid catalyst such as acetic acid, $TiCl_4$ or p-toluenesulfonic acid.

Thereafter, compound (VII) as obtained above is reacted with compound (VIII) in the presence of, or absence of a suitable condensing agent such as Lewis acids, to obtain the pyridine compound of the formula (II). This reaction may be carried out in the presence of, or absence of the reaction-inert solvent as listed above. However, this reaction may preferably carried out in the absence of a solvent. This reaction may be carried out at a temperature of 0° C. to 200° C., preferably, from 60° C. to 150° C. for 30 minutes to 48 hours, preferably 10 hours to 20 hours.

In addition, the beta-keto esters (V) and the substituted benzaldehydes (VI) which can be used herein may be either already known or may be prepared by known methods. For example, the beta-keto esters (V) may be prepared according to the reported methods as shown in, for example, (1) D. Scherling, *J. Labelled Compds. Radiopharm.*, 1989, 27, 599; (2) C. R. Holmquist and E. T. Roskamp, *J. Org. Chem.*, 1989, 54, 3258; (3) S. N. Huckin and L. Weiler, *J. Am. Chem. SC.*, 1974, 96, 1082; (4) *J. C. S. Perkin I*, 1979, 529; and (5) *Synthesis*, 1986, 37; *J. C. S. Chem. Commun.*, 1977, 932).

Preparation Method B-II:

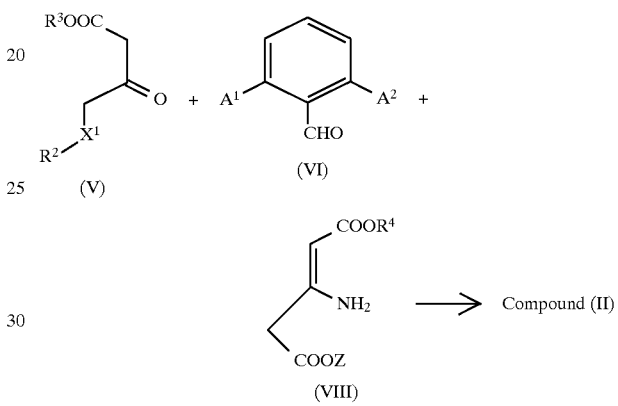

(wherein all the symbols are as already defined)

This method utilizes the three components Hantzsch reaction. In a typical procedure, the beta-keto ester (V), the substituted benzaldehyde (VI) and compound (VIII) may be heated together in a suitable reaction-inert solvent as listed above (preferably lower alkanols such as methanol and ethanol). Preferably, a small amount of a lower alkanoic acid such as acetic acid is added as catalyst. The reaction mixture may be heated at 80° C. to 200° C., preferably from 100° C. to 140° C. for 30 minutes to 1 week, usually 24 hours to 96 hours.

Preparation Method B-III:

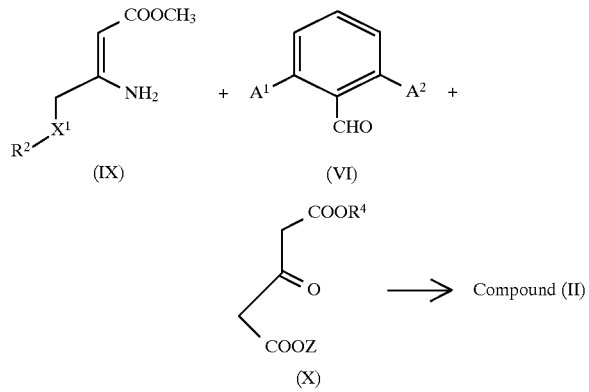

(wherein all the symbols are as already defined)

This method also utilizes the three components Hantzsch reaction as mentioned above. The reaction conditions similar to the above can be also used in this method.

The compound (IX), enamine may either be known compounds or may be prepared by known methods. For example, the enamine compounds (IX) may be prepared by reacting the beta-keto ester (V) with ammonia. More specifically, the beta-keto ester (V) may be dissolved in a suitable solvent as listed above. Excess amount of ammonia gas is introduced into the solution at a temperature of 0° to 60° C. Alternatively, a solution containing ammonia dissolved in the above solvent is added to the solution containing the beta-keto ester (V), and the resultant mixture is reacted at a temperature of 0° to 60° C., to obtain compound (IX). In this method, it is easier to modify the moiety —X—$R^2$ to obtain the dihydropyridine compounds of formula (I) having a desired —$CH_2$—X—$R^2$ moiety attached to the 6 position of the pyridine ring of the dihydropyridine (I).

The compounds of formula (I), and the intermediates shown in the above Preparation Methods can be isolated and purified by conventional procedures, such as recrystallization or chromatographic purification.

As the dihydropyridine compounds of this invention possess at least one asymmetric center, they are capable of occurring in various stereoisomeric forms or configurations. Hence, the compounds can exist in separated (+)- and (−)-optically active forms, as well as in racemic or (±)-mixtures thereof. The present invention includes all such forms within its scope. Individual isomers can be obtained by known methods, such as optically selective reaction or chromatographic separation in the preparation of the final product or its intermediate.

Insofar as the dihydropyridine compounds of this invention are basic compounds, they are capable of forming a wide variety of different salts with various inorganic and organic acids.

The acids which are used to prepare the pharmaceutically acceptable acid addition salts of the aforementioned dihydropyridine base compounds of this invention of formula (I) are those which form non-toxic acid addition salts, i.e., salts containing pharmaceutically acceptable anions, such as the chloride, bromide, iodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, p-toluenesulfonate and pamoate (i.e., 1.1'-methylene-bis-(2-hydroxy-3-naphthoate))salts. The acid addition salts can be prepared by conventional procedures.

The dihydropyridine compounds of the present invention of formula (I) exhibit significant bradykinin receptor-binding activity and therefore, are of value in the treatment of a wide variety of clinical conditions in mammals, especially man. Such conditions include inflammation, cardiovascular disease, pain, common cold, allergies, asthma, pancreatitis, burns, virus infection, head injury, multiple trauma and the like.

Therefore, these compounds are readily adapted to therapeutic use as bradykinin antagonists for the control and/or treatment of any of the aforesaid clinical conditions in mammals, including humans.

The activity of the dihydropyridine compounds of the present invention, as bradykinin antagonists, is determined by their ability to inhibit the binding of bradykinin at its receptor sites in IMR90 cells which express $B_2$ receptor or A431 cells employing radioactive ligands.

The bradykinin antagonist activity of the dihydropyridine compounds is evaluated by using the standard assay procedure described in, for example, Baenziger N. L., Jong Y-J. I., Yocum S. A., Dalemar L. R., Wilhelm B., Vaurek R., Stewart J. M., Eur. J. Cell Biol., 1992, 58, 71–80. This method essentially involves determining the concentration of the individual compound required to reduce the amount of radiolabelled bradykinin ligands by 50% at their receptor sites in rat, guinea pig or monkey tissues, or A431 or IMR90 cells, thereby affording characteristic $IC_{50}$ values for each compound tested.

More specifically, the assay is carried out as follows. First, rat, guinea pig or monkey ileum tissues are minced and suspended in 25 mM piperazine-N,N'-bis (2-ethanesulfonic acid (PIPES) buffer (pH 6.8) containing 0.1 mg/ml of soybean trypsin inhibitor. Then, the tissues are homogenized using a Polytron homogenizer at setting #6 for 30 seconds, and centrifuged at 30,000×g for 20 minutes. The pellets are homogenized with the same buffer, and recentrifuged. The tissue pellets, IMR90 cells or A431 cells are suspended in 25 mM PIPES buffer (pH6.8,) containing 1.25 mM dithiothreitol, 1.75 μg/ml bacitracin, 125 μM o-phenanthroline, 6.25 μM captopril, 1.25 mg/ml bovine serum albumin (BSA), to prepare tissue/cell suspensions. Then, 10 μl of test compound solution dissolved in phosphate buffered saline (PBS, pH 7.5) containing 2% DMSO (final) and 0.1% BSA (w/v) or 10 μl of 12.5 μM bradykinin in PBS (pH 7.5) containing 0.1% BSA (w/v) are placed in a reaction 96-well plate. 15 μl of 8.3 nM [3H]bradykinin are added to the compound solution or bradykinin solution in the 96-well plate. Finally 100 μl of the tissue or cell suspension are added to the mixture in the plate, and incubated at 25° C. for 1 hour. After incubation, the resultant product in the reaction plates is filtered through 0.1% polyethylenimine presoaked LKB filermat. The filtrate is washed using a Skatron auto cell harvester. The tissue bound radioactivity is determined using a LKB betaplate counter. The $IC_{50}$ value is determined using the equation:

$$\text{Bound} = B_{max}/(1+[I]/IC_{50})$$

wherein [I] means the concentration of the test compound.

Some compounds prepared in the Working Examples as described below were tested by this method, and showed an $IC_{50}$ value of 10 nM to 1 μM with respect to inhibition of binding at its receptor.

The dihydropyridine compounds of formula (I) of this invention can be administered via either the oral, parenteral or topical routes to mammals. In general, these compounds are most desirably administered to humans in doses ranging from 0.3 mg to 750 mg per day, preferably from 10 mg to 500 mg per day, although variations will necessarily occur depending upon the weight and condition of the subject being treated, the disease state being treated and the particular route of administration chosen. However, for example, a dosage O that is in the range of from 0.06 mg to 2 mg per kg of body weight per day is most desirably employed for the treatment of inflammation.

The bradykinin antagonist activity of the dihydropyridine compounds in vivo is evaluated by a plasma leakage test. This test essentially involve determining the concentration of the individual compound required to reduce by 50% the amount of bradykinin-induced plasma leakage in rat urinary bladder, thereby affording characteristic $ED_{50}$ values for each compounds tested.

More specifically, the assay is carried out as follows. 3.5-week old male Sprague-Dawlew rats are purchased from Charles River Japan Inc. The rats are fed on stock diet (CRF from Charles River Japan, Inc.) and maintained under the standard conditions (temperature, 23±1° C. and humidity 55±5%) for at least 3 days. The rats are fasted overnight prior to the experiments. Each test group consists of 5 rats.

Bradykinin, purchased from Peptide Ins., is dissolved in the physiological saline (0.9% sodium chloride) at a concentration of 10 nmol/ml. The test dihydropyridine compounds are dissolved or suspended at different concentrations in the physiological saline solution containing 10 mg/ml Evans blue (Wako Pure Chemical, Japan).

Captopril (5 mg/kg of body weight) is intraperitoneally (i.p.) injected to the rats, and 20 min later the rats are anesthetized by an administration of Nembutal (Abbott) (2.5 mg/kg of body weight). 5 min later, the test compound solution containing Evans blue is intravenously (i.v.) injected to the rats at a dose of 3 ml/kg of body weight. Another 5 min later, bradykinin is i.v. injected at a dose of 10 nmol/kg body weight. Thereafter, the rats are killed by dislocation of the neck and the urinary bladders are obtained. The urinary bladders are individually treated with 1 ml of formamide at 60° C. for at least 16 hours to extract Evans blue from the tissue. The absorvance of the extract is measured spectrophotometrically at 605 nm to determined the dye concentration. The effect of the individual test compound is calculated as a percentage of the amount of Evans blue leaked into the urinary bladder as compared to the control (saline for the test compounds).

The dihydropyridine compounds of formula (I) of this invention can be administered via either the oral, parenteral or topical routes to mammals. In general, these compounds are most desirably administered to humans in doses ranging from 0.3 mg to 750 mg per day, preferably from 10 mg to 500 mg per day, although variations will necessarily occur depending upon the weight and condition of the subject being treated, the disease state being treated and the particular route of administration chosen. However, for example, a dosage level that is in the range of from 0.06 mg to 2 mg per kg of body weight per day is most desirably employed for the treatment of inflammation.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral-pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

EXAMPLES

The present invention is illustrated by the following examples. However, it should be understood that the invention is not limited to be specific details of these examples. Melting points were taken with a Buchi micro melting point apparatus and uncorrected. Infrared Ray absorption spectra (IR) were measured by a Shimazu infrared spectrometer (IR-470). $^1$H and $^{13}$C nuclear magnetic resonance spectra (NMR) were measured in $CDCl_3$ by a JEOL NMR spectrometer (JNM-GX270, 270 MHz) unless otherwise indicated and peak positions are expressed in parts per million (ppm) downfield from tetramethylsilane. The peak shapes are denoted as follows: s, singlet; d, doublet; t, triplet; m, multiplet; br, broad.

Example 1

Dimethyl 4-(2,6-dichlorophenyl)-6-(2-phenylethyl)-2-{2-(4-methyl-1-piperazinyl)ethyl}-1,4-dihydropyridine-3,5-dicarboxylate A. Dimethyl 4-(2,6-dichlorophenyl)-6-(2-phenylethyl)-2-(1-oxo-1-methoxy-2-propen-2-yl)-1,4-dihydropyridine-3,5-dicarboxylate Dimethyl 4-(2,6-dichlorophenyl)-2-methoxycarbonylmethyl-6-[2-(phenyl)ethyl]-1,4-dihydropyridine-3,5-dicarboxylate (588 mg, 1.135 m mol) and N-methylpiperazine (0.132 ml, 1.19 m mol) were dissolved in acetic acid (3 ml) and to the solution was added paraformaldehyde. The mixture was stirred at room temperature overnight. The mixture was concentrated in vacuo and partitioned between $CH_2Cl_2$ (50 ml) and aqueous $NaHCO_3$ solution (20 ml). The aqueous layer was extracted with $CH_2Cl_2$ (30 ml). The combined organic layer and the extract were washed with brine (10 ml), dried ($MgSO_4$), and concentrated in vacuo to give a yellow oil. This was crystallized from ethyl acetate and isopropyl ether gave a yellow solid (270 mg, 50.9%). Second crop was obtained from the mother liquid (78 mg, 14.7%). $^1$H NMR ($D_2O$) δ7.35-7.16 (m, 7H), 7-05-6.97 (m, 1H), 6.21 (br.s, 1H), 6.06 (s, 1H), 5.52 (br.s, 1H), 5.43 (br.s, 1H), 3.73 (s, 3H), 3.57 (s, 3H), 3.46 (s, 3H), 3.10-2.80 (m, 4H).

B. Dimethyl 4-(2,6-dichlorophenyl)-6-(2-phenylethyl)-2-{2-(4-methyl-1-piperazinyl)ethyl}-1,4-dihydropyridine-3,5-dicarboxylate To a suspension of the above conjugated ester (270 mg, 0.509 m mol) in methanol (8 ml) was added N-methyl piperazine (0.189 mnl, 1.7 m mol) and heated until all solid dissolved. The mixture was allowed to stand at room temperature overnight. The mixture was concentrated in vacuo and purified by a silica gel column (10 g), eluted with $CH_2Cl_2$ to recover the starting material, dimethyl 4-(2,6-dichlorophenyl)-2-methoxycarbonylmethyl-6-[2-(phenyl)ethyl]-1,4-dihydropyridine-3,5-dicarboxylate (100 mg, 21.4%) and then eluted with $CH_2Cl_2$-methanol-triethylamine (60:2:0.5) to give the desired Mannich coupling product (230 mg, 71.8 %) as white solids. Without further purification, the product (96 mg, 0.152 m ml) was suspended in 1,4-dioxane (1.2 ml) and 2N NaOH (0.4 ml, 0.8 mmol) was added. After stirring for 1 hr, 10% $NaH_2PO_4$ solution (10 ml) was added. The whole was extracted with $CH_2Cl_2$ (10 ml×3) and washed with brine (5 ml). The solution was dried over $MgSO_4$ and concentrated in vacuo to give a yellow solid (92 mg). This was suspended in toluene (3 ml) and stirred at reflux for 1 hr. Chromatography on silica gel (2g) eluted with $CH_2Cl_2$-methanol (10:1) gave a yellow oil. Crystallization from isopropanol gave a white solid (8 mg, 9% yield).

mp 156.0°–157.2° C. $^1H$ NMR ($CDCl_3$) δ 10.11 (s, 1H), 7.33-7.17 (m, 7H), 6.99 (t, J=8.1 Hz, 1H), 5.98 (s, 1H), 3.56 (s, 3H), 3.52 (s, 3H), 3.10-2.25 (m, 19H). IR (KBr) 1685, 1646

Example 2

Dimethyl 4-(2,6-dichlorophenyl)-6-[2-(2-methoxyphenyl)ethyl]-2-{2-(4-methyl-1-piperazinyl)ethyl}-1,4-dihydropyridine-3,5-dicarboxylate-hydrochloride This was prepared by a procedure similar to that described in Example 1, as a white solid.

mp 201°–202.4° C. (dec.) $^1H$ NMR (free base, $CDCl_3$) δ 9.72 (br. s, 1H), 7.30-7.15 (m, 4H), 6.82-7.02 (m, 3H), 5.97 (s, 1H), 3.83 (s, 3H), 3.54 (s, 3H), 3.51 (s, 3H), 3.15-2.19 (m, 19H). $^1H$ NMR (DMSO-d6) δ9.19 (s, 1H), 7.34 (d, J=8.1 Hz, 2H), 7.23-7.11 (m, 3H), 6.97-6.83 (m, 2H), 5.81 (s, 1H), 3.76 (s, 3H), 3.37 (s, 3H), 3.40-2.99 (m, 15H were overlapped with $H_2O$ signal in DMSO), 2.70–2.97 (m, 7H). IR (KBr) 1697, 1686

Example 3

Dimethyl 4-(2,6-dichlorophenyl)-2-[4-(3-guanidinylpropyl)-1-piperazinyl]carbonylmethyl-6-(2-phenylethyl)-1,4-dihydropyridine-3,5-dicarboxylate dihydrochloride A. Dimethyl 4-(2,6-dichlorophenyl)-2-[4-(3-hydroxypropyl)-1-piperazinyl]carbonylmethyl-6-(2-phenylethyl)-1,4-dihydropyridine-3,5-dicarboxylate hydrochloride A solution of dimethyl 4-(2,6-dichlorophenyl)-2-methoxycarbonylmethyl-6-(2-phenylethyl)-1,4-dihydropyridine-3,5-dicarboxylate (1.78 g, 3.44 mmol) in dioxane (14 ml) was treated with 2 N aq. sodium hydroxide (3.5 ml) at room temperature for 2 h. The reaction was quenched with 20% aq. $NaH_2PO_4$ (20 ml) and acidified with 2 N aq HCl to pH ~3, then extracted with $CH_2Cl_2$ (40 ml×3). The combined organic extracts were dried over anhydrous magnesium sulfate and concentrated in vacuo. The resulting residue was dissolved in $CH_2Cl_2$ (23 ml ) and treated with 1-ethyl-3-(3-dimethyl-aminopropyl)-carbodiimide hydrochloride (988 mg, 5.15 mmol) at 0° C. After stirring at 0° C. for 5 minutes under nitrogen atmosphere, 1-(3-hydroxypropyl)piperazine (506 mg, 3.44 mmol) was added into the mixture at 0° C. The mixture was then stirred at room temperature under nitrogen atmosphere for 13 h. The whole was partitioned between $CH_2Cl_2$ (200 ml) and water (40 ml) and then washed with aq. $K_2CO_3$ solution and brine. The organic solution was dried over anhydrous magnesium sulfate and concentrated in vacuo. Chromatography on silica gel (50 g) eluted with $CH_2Cl_2$:MeOH=100:1 to 10:1 gave a yellow solid (1.49 g, 69% yield). 80 mg of the product was treated with 5% methanol HCl solution (0.3 ml) and concentrated in vacuo. Crystallization of the residue from ethanol-diisopropyl ether gave a pale solid (79 mg, 93% yield).

mp (HCl salt): 258.1°–259.6° C. $^1H$-NMR ($CDCl_3$, free base): δ 7.90 (br s, 1H), 7.40 - 7.12 (m, 7H), 7.00 (t, J=7.8 Hz, 1H), 5.99 (s, 1H), 4.70 - 4.40 (m, 1H), 4.22 (d, J=15.0 Hz, 1H), 3.87 - 3.45 (m, 7H), 3.56 (s, 3H), 3.55 (s, 3H), 3.03 -2.78 (m, 4H), 2.69-2.39 (m, 6H). $^1H$-NMR (DMSO-$d_6$):δ 10.82 -10.44 (m, 1H), 9.45 -9.15 (m, 1H), 7.41-7.09 (m, 8H), 5.86 (s, 1H), 4.97 - 4.57 (m, 1H), 4.40 - 3.95 (m, 3H), 3.65-2.41 (m, 21H), 1.95 - 1.75 (m, 2H). IR (HCl salt, KBr): 3440, 1690, 1645, 1620, 1580 $cm^{-1}$.

B. Dimethyl 4-(2,6-dichlorophenyl)-2-[4-(3-aminopropyl)-1-piperazinyl]carbonylmethyl-6-(2-phenylethyl)-1,4-dihydropyridine-3,5-dicarboxylate dihydrochloride To a stirred solution of dimethyl 4-(2,6-dichlorophenyl)-2-[4-(3-hydroxypropyl)-1-piperazinyl]carbonylmethyl-6-(2-phenylethyl)- 1,4-dihydropyridine-3,5-dicarboxylate (1.41 g, 2.24 mmol) in $CH_2Cl_2$ (16 ml) was added triethylamine (1.25 ml, 8.94 mmol) and methanesulfonyl chloride (0.43 ml, 5.59 mmol) at 0° C. The mixture was stirred at 0° C. for 4 h. The whole was partitioned between $CH_2Cl_2$ (200 ml), and aq. $K_2CO_3$ solution (40 ml) and then the organic layer was washed with brine, dried over anhydrous magnesium sulfate and concentrated in vacuo to afford a yellow oil (1.85 g). Without purification, the product was dissolved in dry DMF (16 ml) and treated with sodium azide (436 mg, 6.71 mmol) at 60° C. oil bath for 14 h. The whole was concentrated in vacuo, and the residue was diluted with water (50 ml), and extracted with $CH_2Cl_2$ (50 ml×2). The combined extracts were washed with brine, dried over anhydrous magnesium sulfate and concentrated in vacuo to afford a yellow oil (1.46 g). Without further purification, a solution of the Product in methanol (15 ml) was hydrogenated in the presence of 10% palladium on carbon (146 mg) for 14 h. The mixture was then filtered through a pad of celite. The filtrate was concentrated in vacuo and the residue was purified by a silical gel column (30 g) eluted with $CH_2Cl_2$:MeOH=50:1 to 10:1 to 10:1+5% $Et_3N$ to give a yellow solid (1.224 g, 87% yield). $^1H$-NMR ($CDCl_3$, free base): δ 8.07 (br. s, 1H), 7.34 - 15 (m, 7H), 7.00 (dd, J=8.4, 7.7 Hz, 1H), 5.99 (s, 1H), 4.14 (d, J=15.0 Hz, 1H), 3.77 (d, J=15.0 Hz, 1H), 3.68 - 3.58 (m, 4H), 3.55 (s, 3H), 3.54 (s, 3H), 3.05 - 2.78 (m, 4H), 2.78 (t, J=6.6 Hz, 2H), 2.52 - 2.32 (m, 6H), 2.25 - 2.08 (m, 2H), 1.72 -1.57 (m, 2H).

90 mg of the product was dissolved in 5% methanolic HCl solution (0.5 ml) and concentrated in vacuo. Crystallization of the residue in isopropyl alcohol-disopropyl ether gave a white solid (54 mg, 57% yield) as the corresponding HCl salt.

mp (HCl salt): 186.1°–187.3° C. $^1H$-NMR (DMSO-$d_6$): δ 8.10 - 7.82 (m, 3H), 7.39 -7.09 (m, 8H), 5.86 (s, 1H), 4.55 - 3.96 (m, 3H), 3.75 - 2.53 (m, 23H), 2.13 - 1.95 (m, 2H). IR (HCl salt, KBr): 1695, 1650, 1620, 1580 $cm^{-1}$.

C. Dimethyl 4-(2,6-dichlorophenyl)-2-[4-(3-guanidinylpropyl)-1-piperazinyl]carbonylmethyl-6-(2-phenylethyl)-1,4-dihydropyridine-3,5-dicarboxylate dihydrochloride Dimethyl 4-(2,6-dichlorophenyl)-2-[4-(3-aminopropyl)-1-piperazinyl]carbonylmethyl-6-(2-phenylethyl)-1,4-dihydropyridine-3,5-dicarboxylate (600 mg, 0.954 mmnol) and N,N'-di(t-butoxycarbonyl-S-methylisothiourea (reference: *J. Med. Chem..,* 36 2956–2963 1993) (304 mg, 1.049 mmol) were dissolved in ethanol (8 ml) and treated with mercury (II) oxide (228 mg, 1.049 mmol) at 40° C. oil bath for 20 h. The mixture was then filtrated and the residue was washed with methanol thoroughly. The combined filtrate and washings were concentrated in vacuo. Chromatography on silica gel (18 g) eluted with ethyl acetate:hexane= 1:5 to 1:1 gave a light yellow solid (773 mg). The product was then treated with trifluroacetic acid 2 ml in 2 ml $CH_2Cl_2$ solution at 0° C. for 30 minutes and at room temperature for another 30 minutes. The mixture was then concentrated in vacuo. The residue was dissolved in methanol (5 ml) and treated with 1N aq. hydrochloric acid (0.5 ml). The whole was concentrated and dried azeotropically with isopropyl alcohol. The residue was then dissolved in methanol and the insoluble materials were filtered off. The filtrate was concentrated and dried in vacuo. The resulting solid was dissolved in 100 ml hot ethyl acetate and insoluble solids were removed by filtration. The solution was then cooled to room temperature and was added in small amount of diethyl ether. The precipitate was collected by suction filtration followed by drying in vacuo at 80° C. to give a pale yellow solid (419 mg, 59% yield).

mp: 164.7°–166.1° C. $^1$H-NMR (DMSO-$d_6$): δ 11.52-11.17 (m, 2H), 9.61 -9.20 (m, 1H), 7.99 - 7.81 (m, 1H), 7.59 - 7.02 (m, 8H), 5.86 (s, 1H), 4.54 - 4.01 (m, 5H), 3.78 - 2.41 (m, 19H), 2.06 - 1.84 (m, 2H). IR (KBr): 1730, 1690 - 1620 (br) $cm^{-1}$.

Example 4

Dimethyl 4-(2chlorophenyl)-6-(2-phenylethyl)-2-(4-methylpiperazin-1-yl)carbonylmethyl-1,4-dihydropyridine-3,5-dicarboxylate This was prepared by a procedure similar to that described in Example 3-A, as a light yellow solid.

mp 137.5°–138.1° C. $^1$H NMR (CDCl$_3$) δ 7.74 (br.s, 1H), 7.37-7.01 (m, 9H), 5.47 (s, 1H), 4.15 (d, J=15.4 Hz, 1H), 3.77 (d, J=15.4 Hz, 1H), 3.65 (s, 3H), 3.64 (s, 3H), 3.73-3.57 (m, 4H), 3.13 -2.87 (m, 4H), 2.43-2.22 (m, 7H). IR (KBr) 1692, 1614

Example 5

Dimethyl 4-(2,6-dichlorophenyl)-6-(2-phenylethyl)-2-{4-[(N-morpholino)methyl]phenylcarbamoylmethyl}-1,4-dihydropyridine-3,5-dicarboxylate This was prepared by a procedure similar to that described in Example 3-A, as a light yellow solid.

mp 146.0°–147.0° C. $^1$H NMR (CDCl$_3$) δ 9.31 (s, 1H), 7.30 (d, J=8.4 Hz, 1H), 7.31-7.20 (m, 11H), 7.01 (t, J=7.8 Hz, 1H), 6.85 (br. s, 1H), 5.99 (s, 1H), 3.78 (d, J=13.5 Hz, 1H), 3.74-3.67 (m, 4H), 3.61 (s, 3H), 3.60 (d, J=13.5 Hz, 1H), 3.55 (s, 3H), 3.48 (br. s, 2H), 3.25 (d, J=13.5 Hz, 1H), 3.02-2.75 (m, 3H), 2.48-2.41 (m, 4H). IR (KBr) 1700

Example 7

Dimethyl 4-(2,6-dichlorophenyl)-2-{4-[3-(4,5-dihydroimidazole-2-yl)propyl]-1-piperazinyl}carbonylmethyl-6-(2-phenylethyl)-1,4-dihydropyridine-3,5-dicarboxylate hydrochloride, hydriodide Dimethyl 4-(2,6-dichlorophenyl)-2-[4-(3-aminopropyl)-1-piperazinyl]carbonylmethyl-6-(2-phenylethyl)-1,4-dihydropyridine-3,5-dicarboxylate (300 mg, 0.477 mmol) and 2-methylthio-2-imidazoline hydriodide (117 mg.0.477 mmol) were dissolved in 5 ml chloroform and stirred at reflux for 22 h. The mixture was then cooled and concentrated in vacuo. The residue was dissolved in 5% methanolic HCl solution (1.3 N, 0.6 ml), the mixture was concentrated and the residue was crystallized from ethanol, ethyl acetate and diethyl ether to give a yellow solid (161 mg, 39% yield).

mp: 167.1°–168.4° C. $^1$H-NMR (DMSO-$d_6$): S 11.20 - 10.78 (m, 1H), 9.44 - 9.12 (m, 1H), 8.41 - 8.29 (m, 1H), 7.40 - 7.10 (m, 8H), 5.86 (s, 1H), 4.51 - 4.01 (m, 3H), 3.60 (s, 4H), 3.43 (s, 3H), 3.39 (s, 3H), 3.73 - 2.52 (m, 17H), 2.05 - 1.86 (m, 2H). IR (KBr): 1670 (br), 1620 $cm^{-1}$.

Example 7

Dimethyl 4-(2,6-dichlorophenyt)-2-[4-(t-butoxycarbonyl)-1-piperazinyl]carbonylmethyl-6-(2-phenylethyl)-1.4-dihydropyridine-3,5-dicarboxylate This was prepared by a procedure similar to that described in Example 3-A, as a white solid.

mp: 183.3°–184.1° C. $^1$H-NMR (CDCl$_3$): δ 7.81 (br. s, 1H), 7.35-7.09 (m, 7H), 7.01 (t, J=8.1 Hz, 1H), 5.99 (s, 1H), 4.24 (d, J=15.0 Hz, 1H), 3.73-3.46 (m, 5H), 3.56(s, 3H 3.55 (s, 3H), 3.46-3.31 (m, 4H), 3.00-2.75 (m, 4H), 1.47 (s, 9H). IR (KBr): 1690, 1630, 1620 $cm^{-1}$.

Example 8

Dimethyl 4-(2,6-dichlorophenyl)-2-[N-methyl-N-(2-dimethylaminoethyl)carbonylmethyl-6-(2-phenylethyl)-1,4-dihydropyridine-3,5-dicarboxylate hydrochloride This was prepared by a procedure similar to that described in Example 3-A, as a light yellow solid.

mp: 186.7°–187.8° C. $^1$H-NMR (DMSO-$d_6$): δ 9.52 (s, 1H), 7.42 - 7.08 (m, 8H), 5.86 (s, 1H), 4.33 d, J=15.9 Hz, 1H), 3.53 -3.23 (m, 1H), 3.42 (s, 3H), 3.37 (s, 3H), 3.32 s, 6H), 3.04 (s, 2H), 2.98 - 2.64 (m, 9H). IR (KBr): 1690, 1650, 1630 $cm^{-1}$.

Example 9

Dimethyl 4-(2,6-dichlorophenyl)-2-[4-(4,5-dihydroimidazole-2-yl)-1-piperazinyl]carbonylmethyl-6-(2-phenylethyl)-1,4-dihydropyridine-3,5-dicarboxylate hydriodide This was prepared by a procedure similar to that described in Example 6, as a white solid.

mp: 239.6°–241.3° C. $^1$H-NMR (DMSO-$d_6$): δ 9.12 (s, 1H), 8.43 (s, 2H), 7.41 - 7.09 (m, 8H), 5.86 (s, 1H), 4.17 (d, J=15.3 Hz, 1H:), 3.43 (s, 3H), 3.38 (s, 3H), 3.79 - 2.40 (m, 17H). IR (KBr): 1695, 1675, 1640, 1580 $cm^{-1}$.

Example 10

Dimethyl 4-(2,6-dichlorophenyl)-2-[N-methyl-N-(2-hydroxyethyl)carbamoylmethyl]-6-(2-phenylethyl)-1,4-dihydropyridine-3,5-dicarboxylate This was prepared by a procedure similar to that described in Example 3-A, as a yellow solid, mp: 85.0°–87.7° C. $^1$H-NMR (CDCl$_3$): δ 8.06 (br. s, 0.4H), 7.81 (br. s, 0.6H), 7.41 - 7.12 (m, 7H), 7.00 (t, J=8.7 Hz, 1H), 6.00, 5.98 (s×2, 1H), 4.13 - 3.45 (m, 6H), 3.56 (s, 3H), 3.54 (s, 3H), 3.21 - 2.59 (m, 7H). IR (KBr): 3450 - 3300 (br), 1695, 1630, 1580 $cm^{-1}$.

Example 11

Dimethyl 4-(2,6-dichlorophenyl)-2-[4-(2-guanidinylethyl)-1-piperazinyl]carbonylmethyl-6-(2-phenylethyl)-1,4-dihydropyridine-3,5-dicarboxylate dihydrochloride This was prepared by a procedure similar to that described in Example 3-C, as a light yellow solid.

mp: 174.0°–175.0° C. $^1$H-NMR (DMSO-$d_6$): δ 8.05 - 7.78 (m, 1H), 7.61 - 7.07 (m, 8H), 5.86 (s, 1H), 4.60 - 2.38 (m, 18H), 3.50 (s, 3H), 3.46 (s, 3H). IR (KBr): 1730, 1680, 1650, 1620 cm$^{-1}$.

Example 12

Dimethyl 4-(2,6-dichlorophenyl)-2-{N-methyl-N-[4-(N-methylpiperidino)]}carbamoylmethyl-6-(2-phenylethyl)-1,4-dihydropyridine-3,5-dicarboxylate hydrochloride This was prepared by a procedure similar to that described in Example 3-A, as a yellow solid.

mp: 202.1°–204.4° C. $^1$H-NMR (CDCl$_3$, free base): δ 7.98 (br.s, ⅔H), 7.89 (br. s, ⅓H), 7.38-7.12 (m, 7H), 7.00 (t, J=8.1 Hz, 1H), 6.00 (s, ⅔₁H), 5.98 (s, ⅓H), 4.32 (d, J=15.0 Hz, 1H), 3.61 (d, J=15.0 Hz, 1H), 3.57 -3.51 (m, 6H), 3.06 -2.72 (m, 10H), 2.29 (s, 2H), 2.25 (s, 1H), 2.19 - 1.50 (m, 6H). $^1$H-NMR (DMSO-$d_6$): δ 9.23 (br.s, 1H), 7.48 - 7.08 (m, 81), 5.86 (s, ⅓H), 5.85 (s, ⅔H), 4.60 -3.96 (m, 2H), 3.53 - 3.25 (m, 9H), 3.19 -2.40 (m, 12H), 2.29 - 1.52 (m, 4H). IR (KBr): 1695, 1620, 1580 cm$^{-1}$.

Example 13

Dimethyl 4-(2,6-dichlorophenyl)-2-(4-acetyl-1-piperazinyl)carbonylmethyl-6-(2-phenylethyl)-1,4-dihydropyridine-3,5-dicarboxylate This was prepared by a procedure similar to that described in Example 3-A, as a light yellow solid.

mp : 99.5°–102.0° C. $^1$H-NMR (CDCl$_3$): δ 7.69, 7.63 (br. s×2, 0.5H×2), 7.37 - 7.14 (m, 7H), 7.07 -6.97 (m, 1H), 6.01, 6.00 (s×2, 0.5H×2), 4.38, 4.32 (d×2, J=15.0 Hz, 0.5H×2), 3.87 - 3.40 (m, 15H), 3.02 - 2.82 (m, 4H), 2.14, 2.10 (s×2, 1.5H×2). IR (KBr): 1698, 1630, 1580 cm$^{-1}$.

Example 14

Dimethyl 4-(2,6-dichlorophenyl)-2-[N-(2-hydroxyethyl)]carbamoylmethyl-6-(2-phenylethyl)-1,4-dihydropyridine-3,5-dicarboxylate This was prepared by a procedure similar to that described in Example 3-A, as a yellow solid.

mp: 192.0°–194.0° C. $^1$H-NMR (CDCl$_3$): δ 7.57 - 7.44 (m, 1H), 7.35 - 7.13 (m, 7H), 7.01 (t, J=8.0 Hz, 1H), 5.99 (s, 1H), 3.81 (d, J=13.2 Hz, 1H), 3.74 - 3.63 (m, 2H), 3.562 (s, 3H), 3.556 (s, 3H), 3.43 -3.31 (m, 2H), 3.08 (d, J=13.2 Hz, 1H), 3.02 -2.68 (m, 4H). IR (KBr): 3465, 3310, 2950, 1683, 1648, 1622 cm$^{-1}$.

Example 15

Dimethyl 4-(2,6-dichlorophenyl)-2-[2-(N-methyl-8-azabicyclo[3,2,1]octan-3-yl)amino] ethylcarbamoylmethyl-6-(2-phenylethyl)-1,4-dihydropyridine-3,5-dicarboxylate, dihydrochloride This was prepared by a procedure similar to that described in Example 3-A, as a light brown solid. free base: $^1$H-NMR (CDCl$_3$): δ 7.60 - 7.49 (m, 1H), 7.42-7.07 (m, 7H), 7.01 (t, J=8.1 Hz, 1H), 5.99 (s, 1H), 3.56 (s, 3H), 3.55 (s, 3H), 3.86 - 2.58 (m, 13H), 2.24 (s, 3H), 2.32- 1.28 (m, 8H). HCl salt:

mp: 170.0°–173.0 ° C. (decomposed) $^1$H-NMR (DMSO-$d_6$): δ 9.53 - 9.23 (m, 2H), 8.28 -8.10 (m, 1H), 7.41 -7.08 (m, 8H), 5.87 (s, 1H), 4.05 - 2.56 (m, 22H), 2.31 -1.70 (m, 8H). IR (KBr): 3415, 2950, 1694, 1653, 1624 cm$^{-1}$.

Example 16

Dimethyl 4-(2,6-dichlorophenyl)-2-(4-methylhomopiperazinyl)carbonylmethyl-6-(2-phenylethyl)-1,4-dihydropyridine-3,5-dicarboxylate, monohydrochloride This was prepared by a procedure similar to that described in Example 3-A, as a light yellow solid. Free base: $^1$H-NMR (CDCl$_3$): δ 8.32 - 8.13 (m, 1H), 7.36 - 7.12 (m, 7H), 6.99 (t, J=8.1 Hz, 1H), 5.99 (s, 1H), 4.15 - 3.82 (m, 2H), 3.76 - 3.51 (m, 4H), 3.55, 3.54, 3.53 (s×3, 6H), 3.08 - 2.75 (m, 4H), 2.68 - 2.49 (m, 4H), 2.37, 2.35 (s×2, 3H), 2.00 - 1.84 (m, 2H). HCl salt:

mp: 217.2°–219.0° C. $^1$H-NMR (DMSO-$d_6$): δ 9.40 - 9.25 (m, 1H), 7.39 - 7.08 (m, 8H), 5.87 (s, 1H), 4.05 - 3.22 (m, 15H), 3.01 - 2.58 (m, 8H), 2.29 - 1.99 (m, 2H). IR (KBr): 3435, 1688, 1655, 1628 cm$^{-1}$.

Preparation 1

Dimethyl 4-(2,6-dichlorophenyl)-2-methoxycarbonylmethyl-6-(2-phenylethyl)-1,4-dihydropyridine-3,5-dicarboxylate

A. Dimethyl 2-amino-1-propene-1,3-dicarboxylate

To a stirred solution of dimethyl acetonedicarboxylate (44.1 ml, 0.3 mole) and p-toluene-sulfonic acid (0.19 g, Immol) in benzene (50 ml) was bubbled NH$_3$ gas for 30 min. The mixture was refluxed with azeotropic removal of water using Dean-Stark trap. The bubbling of NH$_3$ gas and azeotropic removal of water was repeated three times. The reaction mixture was diluted with benzene and filtered through a celite pad. The filtrate was concentrated to give an amber color oil (50.75 g). The product was disssolved in diethylether (50 ml) and then hexane was added until the mixture became slightly turbit, and stirred slowly overnight to afford a white solid. This precipitate was collected by suction filtration and washed once with 1/1 mixture of ether/hexane to give a white solid (44.55 g, 86%), mp 47°–50° C. $^1$H NMR (CDCl$_3$) δ 4.58 (s, 1H), 3.73 (s, 3H), 3.64 (s, 3H), 3.16 (s, 2H).

B. Methyl 2-(2,6-dichlorophenylmethylidene)-3-oxo-5-phenylpentanoate

A mixture of methyl 3-oxo-5-phenylpentanoate (10 g, 48.5 mmol), 2,6-dichlorobenzaldehyde (8.486 g, 48.5 mmol), acetic acid (0.56 ml, 9.7 mmol), and piperidine (0.24 ml, 2.42 mmol) in benzene (100 ml) was refluxed with azeotropic removal of water for 3 h. After cooling down the mixture, the whole was washed with water, NaHCO$_3$ aqueous solution, and brine. The mixture was dried over Na$_2$SO$_4$ and evaporation of the solvent afforded a crude viscous oil, which was used for subsequent reaction without purification. $^1$H NMR data indicated that this was 1:1 mixture of E and Z isomers. $^1$H NMR (CDCl$_3$) δ 7.56 and 7.60 (each s, total 1H), 7.20 (m, 8H), 3.59 and 3.83 (each s, total 3H), 3.14-2.83 (m, 4H),.

C. Dimethyl 4-(2,6-dichlorophenyl)-2-methoxycarbonylmethyl-6-[2-(phenyl)ethyl]-1,4-dihydropyridine-3,5-dicarboxylate A mixture of methyl 2-(2,6-dichlorophenylmethylidene)-3-oxo-5-phenylpentanoate (the crude product from the preceding experiment) and dimethyl 2-amino-1-propene-1,3-dicarboxylate (8.4 g, 48.5 mmol) was heated without solvent at 120° C. for 18 h. TLC showed a strong fluorescent spot at Rf=0.3 (dichloromethane/ethyl acetate: 24/1). This whole was chromatographed on silica gel (1.5 kg ) to yield 3.93 g of product. The slightly less pure product (2 g) was also obtained. $^1$H NMR (CDCl$_3$) δ 7.23 (m, 7H), 6.99 (t, J=8.6 Hz, 1H), 6.93 (br. s, 1H), 5.98 (s, 1H), 3.70 (s, 3H), 3.68 (ABq, J=17Hz, 2H), 3.58 (s, 3H), 3.52 (s, 3H), 2.91 (m, 4H).

Preparation 2

4-(N-morphorinomethyl) aniline

A. 4-(N-morphorinomethyl)nitrobenzene

To a solution of 4-nitrobenzylbromide (24.97 g, 115.6 mmol) in acetone (250 ml) was added K$_2$CO$_3$ (19.17 g, 138.7 m mol) and cooled to 10° C. under nitrogen atmosphere. To the mixture was added a solution of morpholine (117.07 g, 127 m mol) in acetone (20 ml) during a period of 15 min under ice bath cooling. The mixture w stirred at room temperature for 2 hr. The starting material was still remained, thus morpholine (2 g, 22.9 mmol) was added and stirred at room temperature for 2 hr. The mixture was concentrated in vacuo and the white residue was suspended in water (300 ml). The insoluble material was collected by suction filtration and washed with water (150 ml) (29 g, wet). The product was recrystallized from isopropanol and dried on air to give a white solid (22.74 g, 88.6% yield). $^1$H NMR (CDCl$_3$) δ 8.18 (d, J=8.8 Hz, 2H), 7.53 (d, J=8.8 Hz, 2H), 3.70-3.76 (m, 4H), 3.59 (s, 2H), 2.44-2.55 (m, 4H).

B. 4-(N-morphorinomethyl)aniline

A mixture of 4-(N-morphorinomethyl)nitrobenzene (22.15 g, 99.8 m ml), Fe (27.86 g, 0.499 mol), NH$_4$Cl (2.67 g, 50 m mol), in ethanol (200 ml) and water (100 ml) was stirred at reflux for 1 hr. The whole was filtrated and the insoluble material was washed with ethanol (200 ml). The combined filtrate and washings were concentrated in vacuo. The residue was dissolved in CH$_2$Cl$_2$ -methanol (5:1, 300 ml), dried over MgSO$_4$ and concentrated in vacuo to give light yellow solids. The product was treated with hot isopropanol and then cooled. The solid was collected by suction filtration to give a pale yellow solid (6.64 g, 34.6%). The second crop was obtained from the mother liquid as a light yellow solid (3.53 g, 18.4%). $^1$H NMR (DMSO-d$_6$) δ 7.12 (d, J=7.7 Hz, 2H), 6.57 (d, J=7.3 Hz, 2H), 5.30 (very br. s, 2H), 3.99 (s, 2H), 3.76 (br. s, 4H), 2.99 (br. s, 4H).

In addition, the chemical structure of the compounds prepared in the examples are summarized in the following Table.

TABLE

| Example # | Y | X$^1$ | X$^2$ | R$^1$ |
|---|---|---|---|---|
| 1 | piperazinyl | CH$_2$ | CH$_2$ | methyl |
| 2 | piperazinyl | CH$_2$ | CH$_2$ | methyl |
| 3 | piperazinyl | | CH$_2$ | CO | 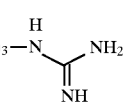 |
| 4 | piperazinyl | CH$_2$ | CO | methyl |
| 5 | NH | CH$_2$ | CO | 4-morpholinomethylphenyl |
| 6 | piperazinyl | CH$_2$ | CO | 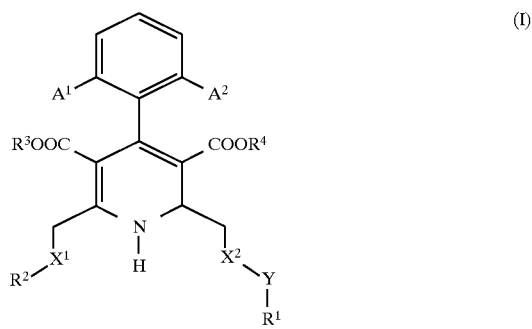 |
| 7 | piperazinyl | CH$_2$ | CO | t-butoxycarbonyl |
| 8 | NCH$_3$ | CH$_2$ | CO | 2-dimethylaminoethyl |
| 9 | piperazinyl | CH$_2$ | CO | 4,5-dihydroimidazol-2-yl |
| 10 | NCH$_3$ | CH$_2$ | CO | 2-hydroxyethyl |
| 11 | piperazinyl | CH$_2$ | CO | 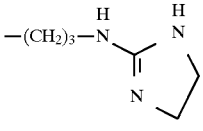 |
| 12 | NCH$_3$ | CH$_2$ | CO | methylpiperidino |
| 13 | piperazinyl | CH$_2$ | CO | acetyl |
| 14 | NH | CH$_2$ | CO | hydroxyethyl |
| 15 | NH | CH$_2$ | CO | [2-(N-methyl-8-azabicyclo[3,2,1]octan-3-yl)amino]ethyl |
| 16 | 4-methyl-homopiperazinyl | CH$_2$ | CO | methyl | wherein R$^2$ is phenyl (provided 2-methoxyphenyl in ex. 2), R$^3$ and R$^4$ are methyl, A$^1$ is Cl (provided H in ex. 4), and A$^2$ is Cl.

I claim:
1. A compound of the formula:

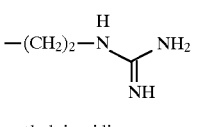

(I)

and its pharmaceutically acceptable salts, wherein each of A$^1$ and A$^2$ is halo or H; X$^1$ is a direct bond, CH$_2$, CO, SO or SO$_2$; X$^2$ is CH$_2$ or CO; Y is piperazinyl-(CH$_2$)$_n$, 2,3,4,5,6,7-hexahydro-1H-1,4-diazepinyl-(CH$_2$)$_n$— or —N(R$^5$)—(CH$_2$)$_n$— wherein R$^5$ is H or C$_{1-4}$alkyl, and n is 0, 1, 2, 3, or 4; R$^1$ is selected from the following:

(a) N-morpholino-C$_{1-4}$alkylpheny, C$_{1-4}$alkoxycarbonyl, C$_{2-5}$acyl, dihydroimidazolyl, formamidino, guanidino or dihydroimidazolylamino, optionally substituted with one or two substituents selected from C$_{1-4}$alkyl, hydroxy and amino;

(b) hydrogen, C$_{1-4}$alkyl optionally substituted with one or two substitutents selected from hydroxy, amino, C$_{1-4}$alkylamino, di-C$_{1-4}$alkylamino, pyridyl, carbamoyl, pyrrolidinocarbonyl, proplyaminocarbonyl, piperidinocarbonyl or morpholinocarbonyl;

(c) piperidinyl optionally substituted on the nitrogen atom with C$_{1-4}$alkyl or C$_{1-4}$alkoxycarbonyl;

(d) C$_{5-14}$cycloalkyl, bicycloalkyl or tricycloalkyl, optionally substituted with one or two substituents selected from oxo, hydroxy, amino, guanidino, C$_{1-4}$alkylamino, di-C$_{1-4}$alkylamino, methoxybenzamido or morpholino;

(e) C$_{7-14}$azacyclo-, azabicyclo- or azatricyclo-alkyl, in which the nitrogen atom optionally has a substituent selected from C$_{1-4}$alkyl, formamidino, dihydroimidazolyl, benzyl optionally substituted with one or two substituents selected from halo and trihalo C$_{1-4}$alkyl, C$_{1-4}$alkyloxycarbonyl optionally substituted with one or two halogen atoms and C$_{2-5}$acyl; and (f) C$_{7-10}$-bicycloalkenyl, benzo C$_{5-7}$cycloalkyl or heterocyclic selected from a monocyclic or bicyclic hydrocarbon group having 4 to 10 carbons atoms and 1 to 3 hetero atoms; with the proviso that when Y is piperazinyl (i) at least one of A$^1$ and A$^2$ is H; X$^2$ is CH$_2$; or R$^1$ is a group selected from group (a); (ii) at least one of A$^1$ and A$^2$ is H and X$^2$ is CH$_2$; (iii) at least one of A$^1$ and A$^2$ is H and R$^1$ is a group selected from (a); (iv) X$^2$ is CH$_2$ and R$^1$ is a group selected from (a); or (v) at least one of A$^1$ and A$^2$ is H, X$^2$ is CH$_2$ and R$^1$ is a group selected from (a); R$^2$ is hydrogen, C$_{1-4}$alkyl, phenyl optionally substituted with one or two substitutents selected from halo, C$_{1-4}$ alkyl, trihalo C$_{1-4}$alkyl and C$_{1-4}$alkoxy, or heterocyclic selected from a monocyclic or bicyclic hydrocarbon group having 4 to 10 carbon atoms and 1 to 3 hetero atoms; and each of R$^3$ and R$^4$ is C$_{1-5}$alkyl.

2. A compound according to claim 1, wherein R$^1$ is selected from group (a); R$^2$ is hydrogen, C$_{1-4}$ alkyl or phenyl optionally substituted with one or two substituents selected from halo, C$_{1-4}$ alkyl, trihalo C$_{1-4}$ alkyl and C$_{1-4}$ alkoxy; and R$^3$ and R$^4$ are each C$_{1-3}$ alkyl.

3. A compound according to claim 2, wherein X$^1$ is CH$_2$, CO or SO; R$^1$ is N-morpholinomethylphenyl, t-butoxycarbonyl, acetyl, guanidinylpropyl, 4,5-dihydroimidazole-2-propyl, 4,5-dihydroimidazol-2-yl or guanidinylethyl.

4. A compound according to claim 1, wherein A$^1$ and A$^2$ are each chloro or fluoro; R$^1$ is selected from group (b); R$^2$ is hydrogen, C$_{1-4}$alkyl or phenyl optionally substituted with one or two substituents selected from halo, C$_{1-4}$ alkyl, trihalo C$_{1-4}$ alkyl and C$_{1-4}$ alkoxy; and R$^3$ and R$^4$ are each C$_{1-3}$ alkyl.

5. A compound according to claim 4, wherein X$^1$ is a direct bond or CH$_2$; R$^1$ is hydrogen, pyridyl, pyrrolidinylcarbonyl, propylaminocarbonyl, hydroxyethyl or dimethylaminopropyl; R$^2$ is hydrogen, phenyl, methoxyphenyl, propyl(methoxy)phenyl, methylphenyl, chlorophenyl, pyridyl or thienyl; and R$^3$ and R$^4$ are both methyl.

6. A compound according a claim 1, wherein A$^1$ and A$^2$ are each chloro or fluoro; X$^1$ is a direct bond or —CH$_2$—; R$^1$ is selected from group (c); R$^2$ is hydrogen, C$_{1-4}$alkyl or phenyl optionally substituted with one or two substituents selected from halo, C$_{1-4}$ alkyl, trihalo C$_{1-4}$ alkyl and C$_{1-4}$ alkoxy; and R$^3$ and R$^4$ are each C$_{1-3}$ alkyl.

7. A compound according to claim 6, wherein R$^1$ is piperidinyl, 1-(butoxycarbonyl)piperidinyl or 1-methylpiperidinyl; and R$^2$ is hydrogen, phenyl, methoxyphenyl, propyl(methoxy)phenyl, methylphenyl, chlorophenyl, pyridinyl or thienyl; and R$^3$ and R$^4$ are both methyl.

8. A compound according to claim 1, wherein A$^1$ and A$^2$ are each chloro or fluoro; X$^1$ is a direct bond or —CH$_2$—; R$^1$ is selected from group (d); R$^2$ is hydrogen, C$_{1-4}$alkyl or phenyl optionally substituted with one or two substituents selected from halo, C$_{1-4}$ alkyl, trihalo C$_{1-4}$ alkyl and C$_{1-4}$ alkoxy; and R$^3$ and R$^4$ are each C$_{1-3}$ alkyl.

9. A compound according to claim 8, wherein R$^1$ is C$_{5-6}$ cycloalkyl, bicyclo[3.2.1]octyl or one of the following:

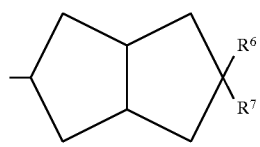

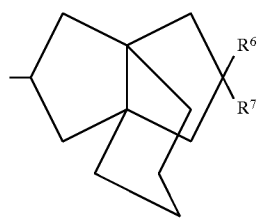

(wherein R$^6$ is hydrogen and R$^7$ is hydroxy, amino, methoxybenzamido, guanidino or morpholino, or R$^6$ and R$^7$ are taken togerther to represent an oxo group); R$^2$ is hydrogen, phenyl, methoxyphenyl, propyl(methoxy)phenyl, methylphenyl, chlorophenyl, pyridinyl or thienyl; and R$^3$ and R$^4$ are both methyl.

10. A compound according to claim 1, wherein A$^1$ and A$^2$ are each chloro or fluoro; X$^1$ is a direct bond or —CH$_2$—; R$^1$ is selected from group (e); R$^2$ is hydrogen, C$_{1-4}$ alkyl or phenyl optionally substituted with one or two substituents selected from halo C$_{1-4}$ alkyl, trihalo C$_{1-4}$ alkyl and C$_{1-4}$ alkoxy; and R$^3$ and R$^4$ are each C$_{1-3}$ alkyl.

11. A compound according to claim 10, wherein R$^1$ is selected from the following groups:

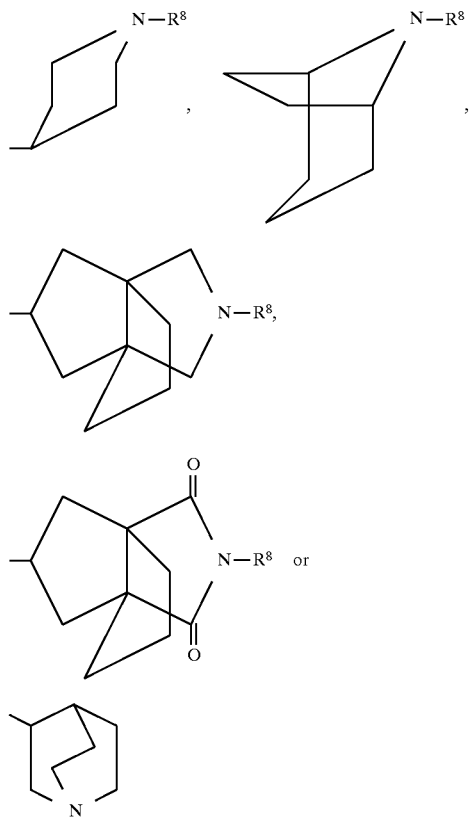

(wherein R$^8$ is hydrogen, formamidino, 4,5-dihydroimidazole-2-yl, C$_{1-4}$ alkyl, benzyl optionally substituted with one or two substituents selected from halo and trihaloalkyl, acetyl or chloroethoxycarbonyl); R$^2$ is hydrogen, phenyl, methoxyphenyl, propyl(methoxy)phenyl, methylphenyl, chlorophenyl, pyridinyl or thienyl; and $R^3$ and $R^4$ are both methyl.

12. A compound according to claim 1, wherein $A^1$ and $A^2$ are each chloro or fluoro; $X^1$ is a direct bond or —$CH_2$—; $R^1$ is selected from group (f); $R^2$ is hydrogen, $C_{1-4}$ alkyl or phenyl optionally substituted with one or two substituents selected from halo, $C_{1-4}$ alkyl, trihalo $C_{1-4}$ alkyl and $C_{1-4}$ alkoxy; and $R^3$ and $R^4$ are each $C_{1-3}$ alkyl.

13. A compound according to claim 12, wherein $R^1$ is norbornenyl, indanonyl or pyrimidinyl; $R^2$ is hydrogen, phenyl methoxyphenyl, propyl(methoxy)phenyl, methylphenyl, chlorophenyl, pyridinyl or thienyl; and $R^3$ and $R^4$ are both methyl.

14. A compound according to claim 1, being one of the following: dimethyl 4-(2,6-dichlorophenyl)-2-[4-(3-guanidinopropyl)-1-piperazinyl]carbonylmethyl-6-(2-phenylethyl)-1,4-dihydropyridine-3,5-dicarboxylate dihydrochloride; dimethyl 4-(2,6-dichlorophenyl)-2-{4-[3-(4,5-dihydroimidazole-2-yl)propyl]-1-piperazinyl}carbonylmethyl-6-(2-phenylethyl)-1,4-dihydropyridine-3,5-dicarboxylate hydrochloride, hydriodide; dimethyl 4-(2,6-dichlorophenyl)-2-[4-(4,5-dihydroimidazole-2-yl)-1-piperazinyl]carbonylmethyl-6-(2-phenylethyl)-1,4-dihydropyridine-3,5-dicarboxylate hydriodide; and dimethyl 4-(2,6-dichlorophenyl)-2-[4-(2-guanidinoethyl)-1-piperazinyl] carbonylmethyl-6-(2-phenylethyl)-1,4-dihydropyridine-3,5-dicarboxylate dihydrochloride.

15. A pharmaceutical composition for the treatment of medical conditions caused by bradykinin, which comprises a therapeutically effective amount of a compound of claim 1 or its pharmaceutically acceptable carrier.

* * * * *